(12) United States Patent
Hofmann et al.

(10) Patent No.: US 9,557,158 B2
(45) Date of Patent: Jan. 31, 2017

(54) SYSTEM AND METHOD FOR DETERMINING THE POSITION OF OBJECTS IN A RADIATION ROOM FOR RADIATION THERAPY

(71) Applicant: LAP GmbH Laser Applikationen, Lüneburg (DE)

(72) Inventors: Karsten Hofmann, Lüneburg (DE); Johann Kindlein, Adendorf (DE)

(73) Assignee: Karsten Hofmann, Lüneburg (DE)

( * ) Notice: Subject to any disclaimer, the term of this patent is extended or adjusted under 35 U.S.C. 154(b) by 0 days.

(21) Appl. No.: 14/567,593

(22) Filed: Dec. 11, 2014

(65) Prior Publication Data

US 2015/0159994 A1  Jun. 11, 2015

(30) Foreign Application Priority Data

Dec. 11, 2013  (EP) .................... 13196634

(51) Int. Cl.
| | | |
|---|---|---|
| *G01B 11/00* | (2006.01) | |
| *A61B 6/08* | (2006.01) | |
| *A61B 6/04* | (2006.01) | |
| *A61B 6/03* | (2006.01) | |
| *A61N 5/10* | (2006.01) | |

(52) U.S. Cl.
CPC ............ *G01B 11/005* (2013.01); *A61B 6/032* (2013.01); *A61B 6/0492* (2013.01); *A61B 6/08* (2013.01); *A61N 5/1049* (2013.01); *A61N 2005/105* (2013.01); *A61N 2005/1059* (2013.01)

(58) Field of Classification Search
CPC .................................. G01B 11/005
USPC ........................................... 356/623
See application file for complete search history.

(56) References Cited

U.S. PATENT DOCUMENTS

| | | |
|---|---|---|
| 5,657,368 A | 8/1997 | Röckseisen |
| 6,272,368 B1 | 8/2001 | Alexandrescu |
| 8,130,384 B2 | 3/2012 | Kindlein et al. |
| 8,235,530 B2 | 8/2012 | Maad |

(Continued)

FOREIGN PATENT DOCUMENTS

| | | |
|---|---|---|
| DE | 297 24 767 U1 | 1/2004 |
| DE | 103 42 201 A1 | 4/2005 |

(Continued)

*Primary Examiner* — Tarifur Chowdhury
*Assistant Examiner* — Omar Nixon
(74) *Attorney, Agent, or Firm* — Young Basile Hanlon & MacFarlane, P.C.

(57) ABSTRACT

A system and method for determining the position of objects in a radiation room for radiation therapy comprises several room lasers arranged in the radiation room, each of which is designed for patient positioning to project at least one laser line onto the surface of a patient located on a patient table in the radiation room. At least one camera detects at least one laser line projected onto the surface of the patient by at least one of the room lasers, and an evaluation and control apparatus determines the coordinate points along the laser line projected onto the surface of patient during a radiation procedure based on measurement values detected by the camera through a real-time triangulation process and compares them with target coordinate points. The coordinate points determined during the radiation procedure may be saved for documentation of the radiation procedure.

19 Claims, 3 Drawing Sheets

(56) References Cited

U.S. PATENT DOCUMENTS

| | | | | |
|---|---|---|---|---|
| 2010/0208274 A1* | 8/2010 | Kindlein | ............... | A61B 6/08 |
| | | | | 356/603 |
| 2011/0135190 A1* | 6/2011 | Maad | ............... | A61B 6/0407 |
| | | | | 382/154 |
| 2012/0300897 A1* | 11/2012 | Flohr | ............... | A61B 6/4014 |
| | | | | 378/9 |

FOREIGN PATENT DOCUMENTS

| EP | 0 687 443 A1 | 12/1995 |
|---|---|---|
| WO | 2009/088407 A1 | 7/2009 |
| WO | 2011/026601 A1 | 3/2011 |
| WO | 2011/071442 A1 | 6/2011 |
| WO | 2012/118228 A1 | 9/2012 |

\* cited by examiner

SYSTEM AND METHOD FOR DETERMINING THE POSITION OF OBJECTS IN A RADIATION ROOM FOR RADIATION THERAPY

CROSS-REFERENCE TO RELATED APPLICATION

This application claims priority to EP 13 196 634.3, filed Dec. 11, 2013, the content of which is incorporated herein in its entirety by reference.

FIELD OF THE DISCLOSURE

The disclosure relates to a system for determining the position of objects in a radiation room for radiation therapy and a corresponding method.

BACKGROUND

Radiation therapy of patients for cancer treatment takes place in radiation rooms. Tumors are thereby irradiated with ionizing radiation by means of radiation devices. The correct positioning of the patient is decisive so that the ionizing radiation hits the tumor optimally. In a computed tomography (CT) room that is separate from the radiation room, the area to be irradiated is localized based on CT images and markings are applied to the patient's body, based on which the patient is then positioned in the radiation room. For this, so-called room lasers are arranged in the radiation room. Room lasers are laser projectors arranged permanently on the ceiling or wall in the radiation room, which generate one or two light arrays. At least three room lasers may be installed, which are pointed at the isocenter of the radiation device. Based on the markings applied to the patient's body and by means of the room lasers, the patient is aligned for the radiation through a suitable moving of a patient table. In particular, the markings applied to the patient's body are brought to overlap with the laser crosses aligned with the isocenter of the radiation device. For the purpose of positioning, only a small area of the respectively projected laser lines around the laser cross is used. Due to the expansion of the light arrays, other objects in the radiation room besides the patient are normally also illuminated by the room lasers.

A device for monitoring the position of a patient receiving radiation is known from DE 103 42 202 A1, in which two or more distance measuring devices measure the distance to respectively one point on the skin of the patient. An evaluation apparatus determines from at least two distance values whether the position of the patient has changed with respect to an initial position. So-called off-axis triangulation can be used for the distance measurement. Another device for capturing the position of an object located in a radiation room is known from DE 297 24 767 U1. A collision of components of the medical apparatus, for example a radiation transmitter, with other objects located in the room should thereby be avoided. A triangulating 3D technique can be used. This known device is also structurally complex since the light transmitters and cameras used for the measurements must also be housed in the radiation room.

BRIEF DESCRIPTION

In DE 103 42 202 A1, only a few individual points on the skin of the patient are captured so that an exact and comprehensive monitoring of the position of the patient body is not satisfactorily possible. Moreover, the device therein is structurally complex, since the distance measuring devices must also be housed in the radiation room. The device in DE 297 24 767 U1 is also structurally complex since the light transmitters and cameras used for the measurements must also be housed in the radiation room.

The above-explained process of patient positioning is based on a subjective assessment by the respective user. The points marked on the skin of the patient for positioning the patient for today's modern radiation therapy no longer meet the accuracy requirements with high doses per radiation fraction and small radiation fields at high field gradients. New imaging methods like cone beam computed tomography (CB-CT), ultrasound or magnetic resonance therapy (MRT) are finding their way into the radiation room and are already being integrated there today. Radiation therapy without multi-modal image registration methods with rigid (RIR) or elastic (deformable DIR) algorithms and image positioning methods is now unthinkable. Nonetheless, current radiation therapy cannot get past the most exact possible initial positioning of the patient with laser lines. Image positioning algorithms use special optimization methods for comparing the three-dimensional (3D) images created before the radiation with a 3D-CT reference position. If the initial patient position is not sufficiently close to the reference position due to faulty patient positioning, these optimization methods can deliver incorrect results. This can lead to incorrect positioning information (displacement vectors) and thus to unplanned irradiation of the patient.

The capturing of CB-CT images before each radiation fraction takes a lot of time and the radiation load on the healthy organs of the patient increases with each image, which can lead to subsequent radiation-induced cancer. Special attention must be paid in this respect to the treatment of children and young adult patients.

There is thus growing need to be able to perform the patient positioning for the radiation and during the radiation with the highest accuracy and without additional radiation load. Moreover, in the case of the modern radiation devices described above with high dose outputs, steep field gradients and short treatment times, there are continuously increasing requirements for the accuracy of the devices used for the radiation. This applies in particular to intensity-modulated radiation therapy (IMRT, VMAT) where the head of a linear accelerator (gantry) used for radiation rotates around the patient during the radiation treatment. For example, in the case of VMAT technology, the modulation of the radiation intensity takes place with a change in the rotational speed of the gantry at certain circular positions and through the different openings of the multi-leaf collimators (MLC). If position deviations occur in the course of the circular movement of the gantry, as can be caused for example by the heavy weight of the gantry, this acts in an impermissible manner on the radiation result. It has also been determined that the position accuracy of a patient table supporting the patient also plays a large role. Even the slightest deviations, as can result for example due to different patient weights, have an adverse effect on the quality of the radiation fraction in today's high-precision radiation procedures.

Based on the above concerns, the invention was developed to desirably provide a system and a method with which the position of objects in a radiation room can be determined for radiation therapy in a structurally simple but yet precise manner. Moreover, impermissible position deviations are desirably detected and subsequent radiation procedures optimized.

Exemplary embodiments of the invention and their variations are explained below in greater detail.

BRIEF DESCRIPTION OF THE DRAWINGS

The description herein makes reference to the accompanying drawings wherein like reference numerals refer to like parts throughout the several views unless otherwise noted, and wherein.

DETAILED DESCRIPTION

Figure 1:
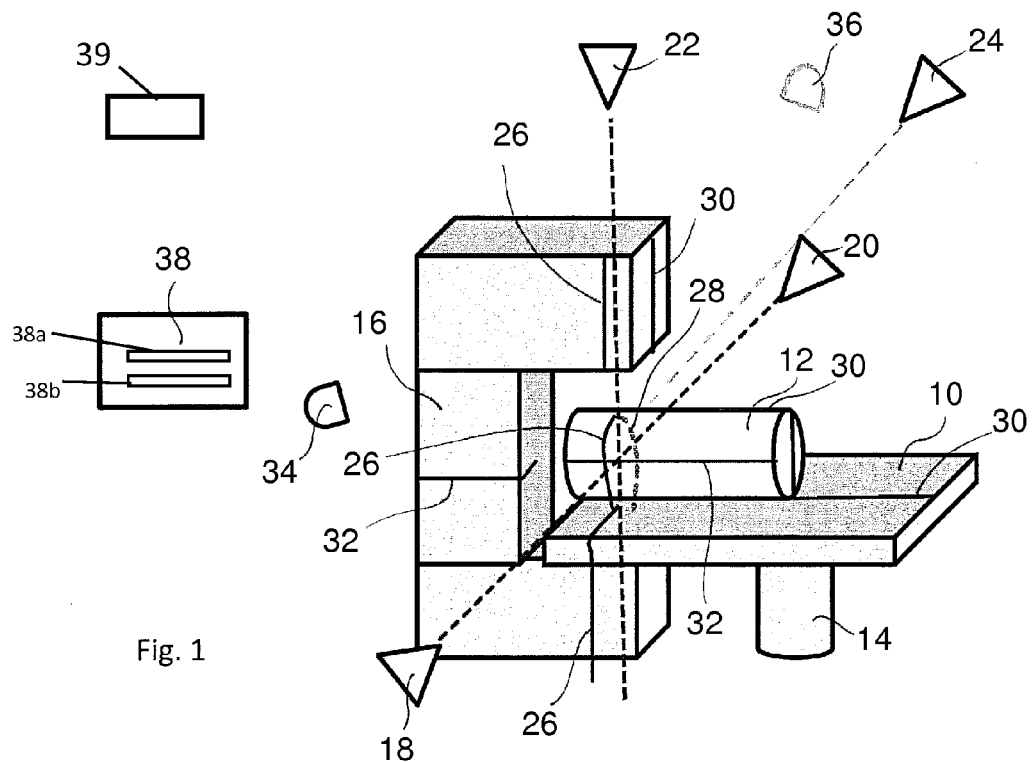
FIG. 1 is a perspective, schematic view of a system according to a first operating state of an implementation of the invention.

The system according to one implementation of the invention can comprise a radiation device and a patient table. A radiation device for cancer therapy of a patient is generally located in a radiation room. The radiation device may be a linear accelerator (LINAC), the head (gantry) of which rotates around the patient table supporting a patient during radiation treatment. According to this implementation, it is suggested that the above-explained room lasers permanently arranged in the radiation room for positioning a patient for radiation be used for further purposes, namely for the position determination of a patient and, if necessary, additional objects in the radiation room. Conventional laser triangulation may be used. At least one laser line, and preferably several laser lines, are at least projected at the patient and at least one laser line, and preferably all laser lines, are recorded by one or more high-resolution cameras. The system is thus structurally simplified through the use of the already present room laser used for patient positioning. Moreover, in contrast to the art described above, not only are few individual points measured on the surface of the patient with respect to their distance from the gantry, but rather the 3D coordinates along the respectively evaluated section of the laser lines are determined by the measuring process of the triangulation. The laser lines can be generated for example by cylindrical lenses. The room lasers can generally transmit laser light in any wavelength ranges, but preferably in the visible range. One or more cameras can be provided in the radiation room so that, in the maximum case, each laser line projected by a room laser is captured by a camera. The field of vision of the cameras is selected such that optionally all laser lines facing the camera are captured by means of a wide angle lens, or only certain sections of interest during use of a lens with correspondingly limited field of vision. In the case of the use of several cameras, a combination of both is also possible.

An evaluation and control apparatus comprises a computer with suitable software, with which the evaluation of the camera images is possible. The room lasers or respectively the cameras can also be controlled with the apparatus and measurement data can be downloaded from the cameras. The 3D coordinates of the laser lines projected in particular on the patient as one of the objects in the radiation room can be determined from this by means of the software. The software can thereby also import Digital Imaging and Communications in Medicine (DICOM) information such as, for example, DICOM-RT information (that is, the information available through the extension of the DICOM 3.0 standard that handles radiotherapy). They can also have in particular a database system. It is also possible to capture several objects located in the radiation room within the framework of the evaluation and determine their relative position with respect to each other.

Through the teachings herein, the real-time position monitoring and detection of a position change using the room lasers already present in the radiation room are allowed in a structurally simple and cost-effective manner. No additional lasers are required for the measurement. Rather, the room lasers are used for further new functionalities, in particular for monitoring the patient position and, if necessary, the position of additional objects during the radiation treatment. A multi-functional, cost-effective and time-effective system is thereby provided. Based on the comparison of the determined coordinate points along the laser lines with target coordinate points, an impermissible deviation in the patient position can be determined and suitable countermeasures can be taken. The target coordinates can be the coordinates measured and saved at the beginning of the radiation treatment after final positioning of the patient. In this case, a change in the patient position with respect to the originally aligned position can thus be determined. Also, the patient positioning, in particular at the beginning of a radiation fraction, is improved herein because the positioning is no longer exclusively based on (relocatable) skin markings but rather on the conformity of entire body contour profiles.

Furthermore, according to the teachings herein, at least the coordinate points determined during the radiation procedure, in particular of patient and gantry, are saved in order to document the radiation procedure. Through the saving of the position data identified during a radiation fraction, exact documentation of the dose received by the patient with each radiation fraction can be compiled with exact localization of the area of affected burden of the radiation. On this basis, the quality of a radiation fraction can be assessed precisely and subsequent radiation fractions can also be adjusted in a suitable manner. In particular, deviations from a target dose received in one radiation fraction can be compensated for in a subsequent radiation fraction.

The measurement of the profile shape of the laser lines lying in the field of vision of the camera can thereby take place for determining the coordinates in the respective sectional plane, preferably in the coordinate system of the radiation device. For this, the existing camera coordinate systems are transformed into a common space coordinate system with the help of a calibration process. As explained, the intersection of three laser planes arranged respectively orthogonally to each other is preferably selected as the point of origin of the space coordinate system. The intersection coordinates determined according to the invention can then be determined in this space coordinate system. If, for example, three laser lines are captured and evaluated with respect to the coordinate points by means of cameras, each of the laser lines delivers one coordinate family. For example, the laser planes generated by the room lasers should intersect in the isocenter of the radiation device, which has for example the coordinates (0, 0, 0) in the space coordinate system. A first laser line then delivers the coordinate values (x, y, 0). A second laser line then delivers the coordinate values (x, 0, z). A third laser line then delivers the coordinate values (0, y, z). The patient position can be determined clearly with this coordinate family.

Since the eye safety of the people located in the radiation room is important, the maximum possible brightness of the laser lines is limited. A relatively poor contrast between the laser lines and the surrounding objects as captured by the camera can thus result. In order to improve the laser line detection in the camera images, optical bandpass filters can be used, which are synchronized for the respective laser wavelength used. Through the use of an optical bandpass filter, the objects surrounding the laser lines can be hidden to a certain degree.

Alternatively or additionally, it is possible that the evaluation and control apparatus switches the respectively controlled room lasers on and off such that the cameras see images of the area respectively captured by the camera with projected laser lines and without project laser lines in quickly alternating succession. Immediately successive images can then be subtracted from each other by the evaluation and control apparatus, in particular pixel by pixel, so that the laser lines emerge as the difference between two immediately successive camera images with very high contrast.

In the case of several projected and evaluated laser lines, the laser lines themselves for example can be projected in a temporally offset manner—timely multiplexing can thus take place. It can thus be ensured that certain cameras always only see one laser line at a time. This could also be achieved in that the different laser lines of lasers are projected with a different wavelength and the respective cameras detect for example only one wavelength through the provision of suitable filters.

Desirably, if two of the used room lasers generate fan-shaped light planes aligned with each other in a coplanar manner in the target scenario, it is also possible to check the coplanarity of these light planes by means of the cameras provided.

According to a further embodiment, the target coordinate points can be determined based on a CT image of the patient made before the radiation treatment and saved in memory of the evaluation and control apparatus. It is then also possible that the target coordinate points were determined from intersection coordinate points of the surface of the patient determined within the framework of the CT image with at least one plane progressing through the center of the area of the patient to be irradiated, preferably with two or three planes located perpendicular to each other and intersecting in the center of the area of the patient to be irradiated.

According to a further design, it is possible that the target coordinate points are determined after the patient has been positioned in the specified radiation position before a radiation procedure with an imaging process (CB-CT, ultrasound), in that coordinate points along the laser lines projected on the surface of the patient are determined by the evaluation and control apparatus based on the measurement values detected by the camera through a real-time triangulation process. The coordinate points determined in this manner may be saved as target coordinate points in the memory apparatus of the evaluation and control apparatus.

The system can also comprise a display apparatus or device, which shows the actual coordinate points determined during a radiation procedure and, optionally, the target coordinate points in real time. The coordinate points can be shown directly or visualized in a suitable manner. For example, fitted lines can be laid through coordinate points.

The evaluation and control apparatus can also be designed to emit a warning signal in the case of an impermissible deviation between the determined coordinate points and the target coordinate points and/or to perform a correction of the patient position by activating movement control of the patient table. The respective parameters are set during patient positioning at the beginning of a radiation fraction. If, in the course of the monitoring of the patient position performed during the subsequent radiation procedure, an impermissible deviation is determined, a warning signal can first be emitted. The warning signal can be optic and/or acoustic and/or haptic. A user can then take manual measures, for example, to reposition the patient or cancel the radiation procedure. Naturally, it is also possible that the evaluation and control apparatus automatically cancels the radiation, for example through an emergency-stop activation. But, fully automatic adjustment of the patient position is also possible where the evaluation and control apparatus activates the travel drives of the patient table based on the measured values such that the measured actual coordinate points and the target coordinate points match again. Tracking thus occurs. A conventional 3D matching algorithm can be used for this tracking.

The evaluation and control apparatus can also be designed to capture a breathing movement or another type of movement of the patient during a radiation procedure through the determination of the 3D coordinates of the laser lines. In this way, the radiation device can be controlled such that radiation only takes place in a specified breathing position or other movement position of the patient. Real-time consideration of how the patient's chest rises during breathing thus takes place during a suitable real-time position evaluation of the flexible patient surface. So-called 4D radiation is possible for this. 4D-CT data can also be used to determine the rise of a patient's chest due to breathing from the measured coordinate points.

According to a further design, the evaluation and control apparatus can be designed to determine the coordinates of a laser line intersecting the surface of the patient at the intersection of a central beam of the radiation device and to determine the focus-skin distance from the coordinates. The focus-skin distance is defined by the distance of the focus or focal point of the radiation device to the surface of the patient along a vector from the focus or focal point of the radiation device to the isocenter (generally the point of origin of the coordinate system). The focus-skin distance is an important parameter in radiation therapy.

According to a further design, at least one of the room lasers projects a laser line onto the surface of the patient table and/or radiation device in the radiation room, at least one camera is designed to detect the laser line projected onto the surface of the patient table and/or radiation device by the at least one room laser, and the evaluation and control apparatus is designed to determine the coordinate points along the laser line projected onto the surface of the patient table and/or radiation device during a radiation procedure based on the measurement values detected by the camera through a real-time triangulation process. According to a further related design, the evaluation and control apparatus is further designed to compare the determined coordinate points along the laser line projected onto the surface of the patient table and/or radiation device with target coordinate points and to emit a warning signal, in particular a collision warning signal, in the case of an impermissible deviation (i.e., a deviation outside defined limits) between the determined coordinate points and the target coordinate points. The target coordinate points can be determined, for example, during the course of the planning of the radiation treatment and saved in the memory apparatus. The evaluation and control apparatus may be further designed to save the coordinate points along the laser line projected onto the surface of the patient table and/or radiation device determined during the radiation procedure in the memory apparatus for documentation of the radiation procedure.

As explained, the head of the radiation device, i.e., the gantry, can be rotated 360° in a fixed plane. During this rotational movement, the heavy weight of the gantry has different effects on the accuracy of the rotational movement in different positions. As mentioned initially, such inaccuracies in the rotational movement lead to undesired impacts on the radiation accuracy. The additional weight of a generally extendible X-ray tube and the opposite-lying image detector contribute to further inaccuracies. The patient table can generally perform both translatory movements as well as rotational movements. Depending on the position and weight of a patient located on the table, deviations from the respectively specified positions are possible, which, as initially explained, also have undesired effects on the radiation result.

In the case of the aforementioned designs, a real-time determination of the position of the radiation device and/or the patient table continues to take place by means of the room lasers. Other objects present in the radiation room can also be monitored in this manner and a collision can be prevented, for example. Alone the coordinates of the respectively projected lines determined by the triangulation process do not yet necessarily provide sufficient information on the position of the object in the room. For this reason, for example, the 3D coordinates of the points on the surface of the object to be monitored, for example a gantry, are desirably known, in particular in the form of 3D computer-aided design (3D-CAD) data or from initial measurements. For example, the gantry rotational angle is determined by a mathematical search algorithm stored in the software of the evaluation and control apparatus, in which the theoretically determined coordinates of virtual laser projection lines have the same values as the coordinates of the laser projection lines determined metrologically by the triangulation process. The more projected lines are evaluated, the faster the position determination can take place. The position of the objects in the radiation room can be determined in real time by an evaluation of the known initial position of the objects in the radiation room as well as their also known 3D degree of mobility and 3D surfaces through the software of the evaluation and control apparatus by means of conventional mathematical processes given the teachings herein.

The metrologically determined position of additional objects in the radiation room besides the patient can also be taken into consideration in the documentation in the memory apparatus so that the radiation dose effectively received by the patient in a radiation fraction can be determined precisely and can be taken into consideration, for example, in the setup of additional radiation procedures.

A further problem area is the assignment of the measured 3D coordinates to a certain object, that is, the question of whether the camera measures laser line coordinates on the object to be measured or on another object. This problem area can be solved in two ways. In a first alternative, the object to be measured can be moved to various positions within the framework of a calibration process and the correspondingly projected laser lines can be received and saved. During a subsequent measurement, the measured lines can be compared with the saved lines and the position present during the measurement is concluded through a matching process based on the empirically performed assignment of certain positions of the object to certain laser lines. According to a second alternative, different surface qualities of the objects, for example different reflectivities, can be evaluated. The application of contrast markings of a different type to different objects is also conceivable in order to be able to differentiate between the different objects within the framework of the evaluation.

According to a further design, at least four room lasers are provided. Of the at least four room lasers, two are arranged on opposite-lying sides of the patient table and project respectively one lateral horizontal laser line and one transverse line onto a patient lying on the patient table. Further, of the at least four room lasers, at least two are arranged above the patient table, one of which projects at least one transversal line onto a patient lying on the patient table, and one of which projects a longitudinal line onto a patient lying on the patient table.

The first and second room lasers arranged laterally to the patient table thus generate two fan-shaped, orthogonal laser light planes. The laser light planes emitted by these two room lasers lying opposite each other and arranged on both longitudinal sides of the patient table are respectively arranged in pairs in a coplanar manner. The third room laser arranged above the patient table and generating the transversal line can, in addition to the fan-shaped laser light plane generating the transversal line, also generate a fan-shaped laser light plane orthogonal to it, which (like the laser light plane of the fourth room laser arranged above the patient table) also generates a longitudinal line on the patient body. The laser light planes of these three room lasers intersect in the isocenter of the radiation device. These room lasers generate three lines on the patient surface: one longitudinal, one transversal and one line horizontally lateral (coronal) from each side. Three crosses are thereby generated on the surface of the patient (laterally left and right as well as on top). The original points of the first three room lasers (left, right and top) can be coplanar. These three room lasers are then arranged in a plane progressing perpendicularly to the longitudinal axis of the patient table.

Just like the third room laser, the fourth room laser can be arranged above the patient table. This fourth room laser, which generates in particular just one laser line, is not arranged with its origin in the same plane progressing perpendicular to the longitudinal axis of the patient table as the other room lasers. It is rather arranged offset in the longitudinal direction of the patient table. But the laser light plane of the fourth room laser also progresses through the intersection of the laser light planes generated by the other room lasers. Moreover, the laser light plane generated by this fourth room laser lies in the same plane as the laser light plane of the third room laser generating the longitudinal line (ceiling laser).

Due to their large spread, the room lasers thereby also each project laser lines on the objects surrounding the patient in the radiation room, such as the radiation device and the patient table. A cross should be able to be projected onto the patient in any position of the radiation device. Since the gantry in its upper (zero) position shadows the third room laser, the fourth room laser takes over the projection of the longitudinal line in this case, so that a cross can nonetheless be mapped on the top side of the patient's body.

It is possible that the lateral first and second room lasers and/or the upper third room laser comprise respectively one laser source, which generates the two orthogonal laser light planes via suitable lenses. But it is also possible that the lateral first and second room lasers and/or the upper third room laser comprise respectively two laser sources, of which each one laser source generates respectively one of the orthogonal laser light planes. In this case, the two laser sources can be arranged in a common housing or even spatially separated in separate housings.

According to a further design, at least two cameras can be provided, which are respectively designed to detect the laser lines projected by at least two room lasers. Desirably, the cameras are high-resolution cameras. They can be, for example, CCD cameras or similar optical sensors. Naturally, more than two such cameras can also be provided.

The system according to one implementation of the invention shown schematically in FIG. 1 comprises a patient table 10. A patient, illustrated in FIG. 1 by a cylinder 12, can be supported by the patient table 10. The patient table 10 sits on the floor via one or more legs 14. By means of drives (not shown), the patient table 10 can be moved both in a translatory manner in the longitudinal direction and transverse direction as well as rotationally around its longitudinal axis and its transverse axis. Moreover, the system has a linear accelerator as radiation device 16, which can be rotated 360° around the patient table 10 according to known techniques.

The system according to FIG. 1 comprises several room lasers permanently arranged in a radiation room in which the patient table 10 and the radiation device 16 are housed. The walls and ceiling of the radiation room are not shown for clarity. A first lateral room laser 18 and a second lateral room laser 20 are attached to the walls of the radiation room on opposing longitudinal sides of the patient table 10. Moreover, a third room laser 22 and a fourth room laser 24, which are fastened on the ceiling of the radiation room by example, are located above the patient table 10. Each of the room lasers 18, 20, 22, 24 can be moved perpendicular to at least one laser line projected by it. The first and second room lasers 18, 20, both arranged laterally, project on one side a respective vertical laser line 26, 28 onto the patient's body 12 and, moreover, onto the patient table 10 and the radiation device 16. The fan-shaped laser light planes generated for this purpose by the lateral room lasers 18, 20 lie in a coplanar manner with respect to each other.

The upper third room laser 22 also generates a light plane progressing in a coplanar manner to it and thus forms a so-called transversal line together with the lateral room lasers 18, 20. The laser light plane of the third room laser 22 generating the transversal line lies in a coplanar manner to the laser light planes of the lateral room lasers 18, 20 generating the vertical laser lines 26, 28. Moreover, one horizontal laser line 32 is projected onto the patient's body 12 as well as the radiation device 16 by each of the laterally-arranged first and second room lasers 18, 20. The fan-shaped laser light planes generated for this purpose by the lateral first and second room lasers 18, 20 also lie in a coplanar manner with respect to each other. The upper third room laser 22 also generates a second laser light plane, which generates a longitudinal line 30 on the patient's body 12 and on the patient table 10 as well as the radiation device 16 in this example. The upper fourth room laser 24 projects, together with the third room laser 22, the longitudinal line 30 onto the patient's body 12 and onto the patient table 10 as well as the radiation device 16. The laser light planes of the third and fourth room lasers 22, 24 forming the longitudinal line 30 lie in a coplanar manner with respect to each other. It can be seen that the room lasers 18, 20, 22 with their origin lie in the same plane progressing perpendicular to the longitudinal axis of the patient table 10. In contrast, the fourth room laser 24 is arranged in the longitudinal direction of the patient table 10 offset with respect to the other room lasers 18, 20, 22. A laser line cross can thereby be projected onto the patient's body 12 in any rotational position of the radiation device 16. The laser light planes of the room lasers 18, 20, 22, 24 intersect in the isocenter of the radiation device 16.

Two high-resolution cameras 34, 36 are included in the illustrated example. The cameras can be, for example, CCD cameras. The cameras 34, 36 are aligned such that they can jointly detect all laser lines projected by the room lasers 18, 20, 22, 24.

An evaluation and control apparatus 38 is connected with the cameras 34, 36 and the room lasers 18, 20, 22, 24 via suitable lines (not shown in greater detail). The evaluation and control apparatus 38 can control the room lasers 18, 20, 22, 24 in order to generate a laser line in the manner explained above. Moreover, the evaluation and control apparatus 38 can download measurement data recorded by the cameras 34, 36. On this basis, the evaluation and control apparatus 38 determines the 3D coordinate points along the laser lines projected onto the surface of the patient's body 12 during a radiation procedure through a real-time triangulation process and compares them with target coordinate points. This can occur in the aforementioned manner. On this basis, the evaluation and control apparatus 38 can take further measures, for example visualizing an impermissible deviation in the aforementioned manner or controlling the patient table 10 in a suitable manner via lines (not shown), in order to reposition the patient's body 12.

Moreover, the evaluation and control apparatus 38 can also evaluate in the aforementioned manner the laser lines projected onto the surface of the patient table 10 and/or onto the surface of the radiation device 16 with respect to their 3D coordinate points. An impermissible deviation can also be determined here and the countermeasures already explained can be used. As mentioned, an impermissible deviation is one that is outside defined limits. The limits would depend upon the procedure being performed and/or the preferences of the treating individual.

As mentioned above, the evaluation and control apparatus 38 may be implemented by a computer. More specifically, the evaluation and control apparatus 38 may be implemented by a computing device with a non-transitory memory device 38a and a processor 38b, such as a central processing unit (CPU), coupled by a bus or other communication path. The methods and/or techniques to implement the functions of the evaluation and control apparatus 38 described herein may be implemented in whole or in part, for example, as a software program/application comprising machine-readable instructions that are stored in the memory that, when executed by a processor, cause a server to perform the functions. Some computing devices may have multiple memories and multiple processors, and the steps described herein may in such cases be distributed using different processors and memories. Use of the terms "processor" and "memory" in the singular thus encompasses computing devices that have only one processor or one memory as well as devices having multiple processors or memories that may each be used in the performance of some but not necessarily all steps.

The methods and/or techniques to implement the functions of the evaluation and control apparatus 38 may also be implemented using hardware in whole or in part. The hardware can include, for example, computers, intellectual property (IP) cores, application-specific integrated circuits (ASICs), programmable logic arrays such as a field-programmable gate array (FPGA) configured as a special-purpose processor, optical processors, programmable logic controllers, microcode, microcontrollers, servers, microprocessors, digital signal processors or any other suitable circuit. The term "processor" herein should be understood as encompassing any of the foregoing hardware, either singly or in combination.

The memory device 38a of the evaluation and control apparatus 38, in addition to storing instructions to control the system to implement the teachings herein, may also save the coordinate points determined during a radiation procedure for documentation of the radiation procedure and, if applicable, for adjustment of additional radiation procedures. The memory device 38a can include Random Access Memory (RAM) or any other suitable type of non-transitory storage device. The memory used to store data as described herein may include another type of device, or multiple devices, capable of storing data for processing by a processor in a computing device now-existing or hereafter developed. The display device 39 capable of displaying data measured and/or calculated herein may be integral with the evaluation and control apparatus 38, or may be coupled thereto with a connector as shown in FIG. 1.

Figure 2:
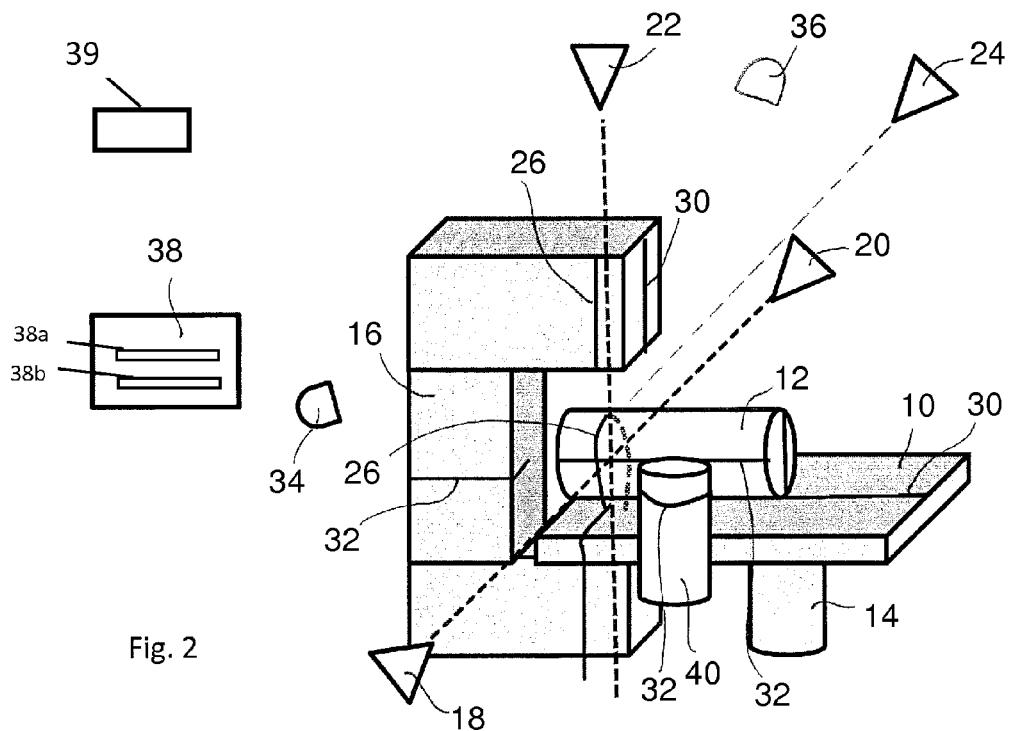
FIG. 2 is a perspective, schematic view of the system of FIG. 1 in a second operating state.

In the operating state shown in FIG. 2, a further object 40 is arranged in the radiation room, wherein the laser line 32 also extends beyond this object 40. This can in turn be determined through identification of the 3D coordinate points by the evaluation and control apparatus 38 and a collision warning can be emitted, for example, if the radiation device 16 were to collide with the object 40 in the course of its rotation. In case of emergency, the radiation procedure can also be interrupted by the evaluation and control apparatus 38 in order to avoid a collision.

Figure 3:
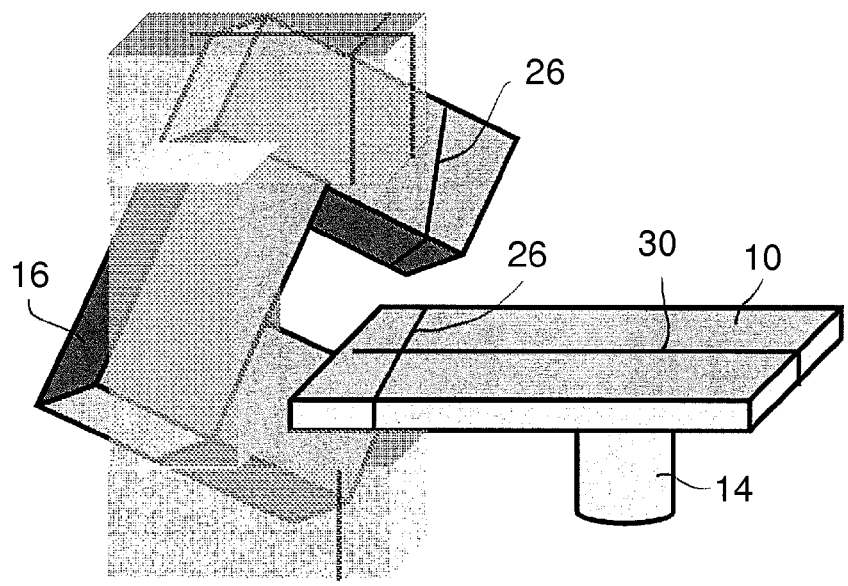
FIG. 3 is a perspective, schematic view of certain components of the system of FIG. 1 in a third operating state.

The impact of a rotation of the radiation device 16 out of the initial position shown partially transparently in FIG. 3 is explained in a simplified representation of the system of FIGS. 1 and 2. It can be seen that in particular the laser line 26 changes with respect to its shape and its position in the room. This can be detected by the evaluation and control apparatus 38 together with the room lasers 18, 20, 22, 24 and the cameras 34, 36. On this basis, the respective rotational angle of the radiation device 16 can be concluded in the aforementioned manner. A deviation caused by the weight of the radiation device 16 can also be determined by the circular movement direction and saved in the memory apparatus for documentation.

Figure 4:
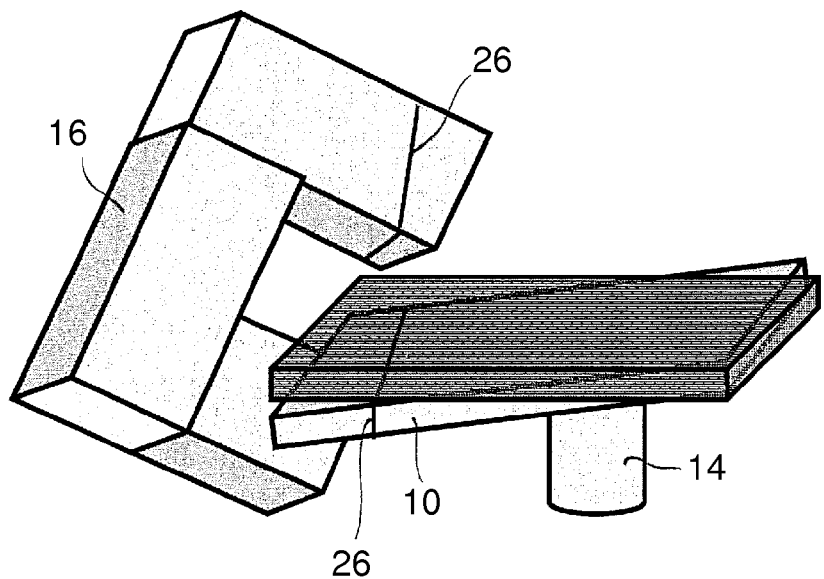
FIG. 4 is a perspective, schematic view of the components of the system of FIG. 3 in a fourth operating state.

FIG. 4 shows the effect of a position change of a patient table 10 with respect to the initial position. The position change is shown partially transparently in FIG. 4. This position change in turn leads to a change in the line shape and position in particular of the laser line 26 and also the laser line 30 (not shown in FIG. 4), which can be determined in the manner according to the invention as illustrated. This deviation can also be documented in the memory device.

Figure 5A:
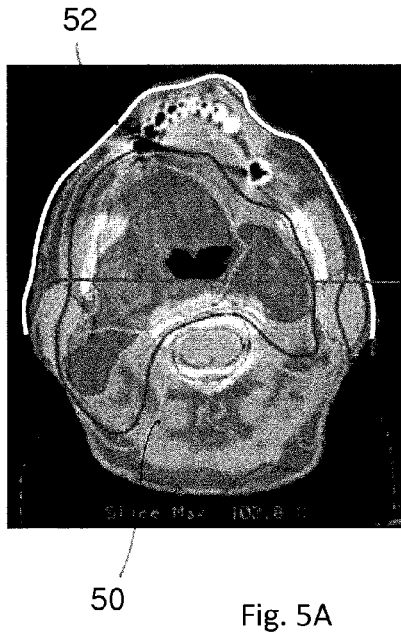
FIGS. 5A and 5B are representative scans of a patient with correct patient positioning.
Figure 5B:
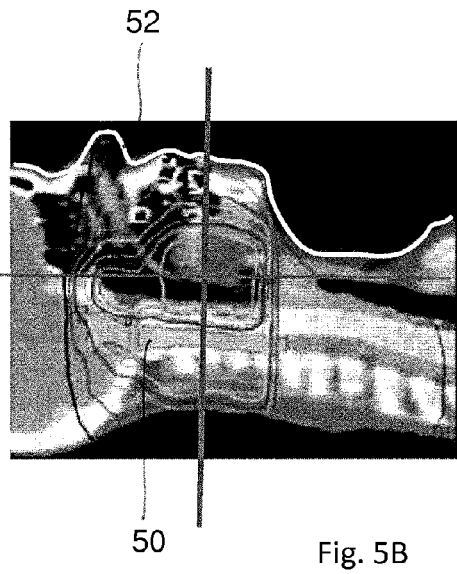
Figure 6A:
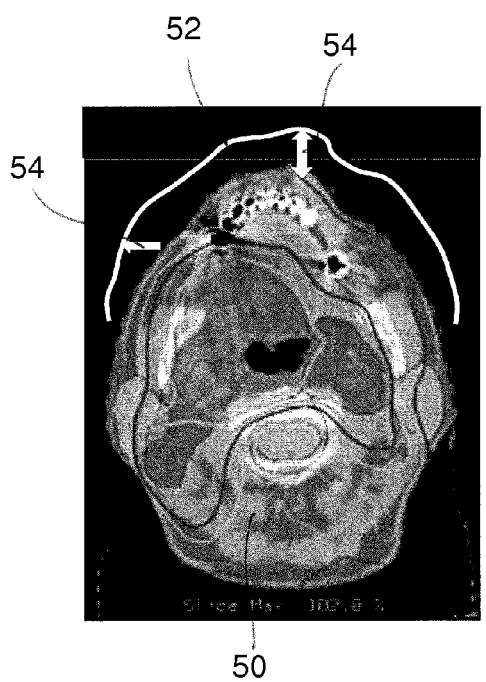
FIGS. 6A and 6B are representation scans of the patient of FIG. 5 with incorrect patient positioning.
Figure 6B:
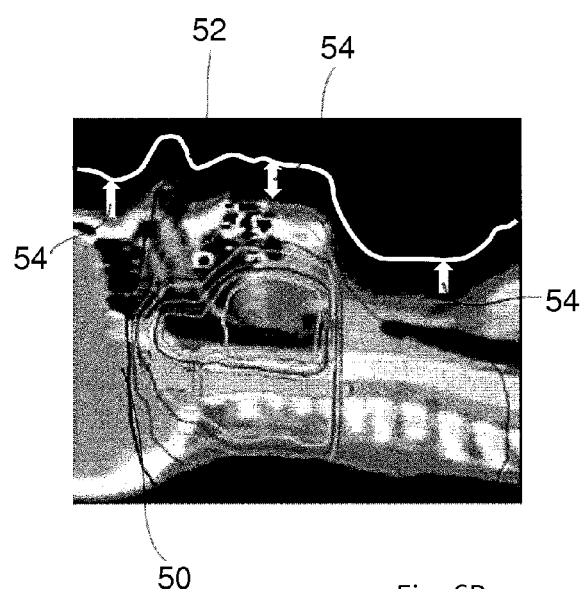

The monitoring of the patient position according to one implementation of the invention will be explained schematically based on FIGS. 5A, 5B, 6A and 6B. A sectional view 50 of a head of a patient originating from a CT image is thereby shown respectively in the left and right image halves. Reference number 52 shows respectively in white a coordinate line determined according to the method or system described herein. FIGS. 5A and 6A show the actually measured surface of the patient's head during the radiation procedure in a transversal cut, while FIGS. 5B and 6B show the actually measured surface of the patient's head during the radiation procedure in a longitudinal cut. The target coordinates for the laser lines 52 are specified respectively through the surface of the patient's head in the CT sectional view 50. The evaluation and control apparatus 38 according to the teachings herein compares the measured coordinate points along the lines 52 with these target coordinates. FIGS. 5A and 5B give the correct position of the patient according to the target coordinates; in particular, the patient's head where the area to be irradiated lies in the isocenter of the radiation device 16. It can be seen in FIGS. 6A and 6B that the measured coordinate points along the laser lines 52 deviate from the target coordinates formed by the surface of the CT section views; in particular, the patient lies too high in the example shown in FIGS. 6A and 6B. The deviation is shown by the arrows 54 in FIGS. 6A and 6B. Through movement of the patient table 10, controlled automatically by the evaluation and control apparatus 38 in at least one implementation, the patient's body can be moved downwards until the coordinates of the laser lines 52 measured in real time match the target coordinates from the CT sectional views.

What is claimed is:

1. A system for determining the position of objects in a radiation treatment room for radiation therapy, comprising:
   several room lasers, each of which is arranged to project at least one laser line onto a surface of a patient located on a patient table;
   at least one camera, each of which is arranged to detect at least one laser line projected onto the surface of the patient by at least one of the several room lasers; and
   an evaluation and control apparatus configured to:
      determine first coordinate points along a laser line projected onto the surface of the patient during a first radiation treatment procedure based on measurement values detected by the at least one camera through a first real-time triangulation process, and compare them with target coordinate points for patient positioning, the evaluation and control apparatus including a memory device in which the first coordinate points determined during the first radiation treatment procedure are saved for documentation of the first radiation treatment procedure, and the first radiation procedure using a target dose; and
      determine second coordinate points along a laser line projected onto the surface of the patient during a second radiation treatment procedure based on measurement values detected by the at least one camera through a second real-time triangulation process, and compare them with target coordinate points for patient positioning, the evaluation and control apparatus configured to use the first coordinate points saved in the memory device to modify the target dose for the second radiation treatment procedure of the patient.

2. The system according to claim 1, wherein the target coordinate points were determined based on a computed-tomography (CT) image of the patient or on another reference image process performed before the first radiation treatment procedure, the target coordinate points stored in the memory device of the evaluation and control apparatus.

3. The system according to claim 2, wherein the target coordinate points were determined from intersection coordinate points of the surface of the patient determined within a framework of the CT image or the reference image process with at least one plane progressing through a center of an area of the patient to be irradiated.

4. The system according to claim 1, wherein the target coordinate points were determined after the patient was positioned with an area to be irradiated in an isocenter of a radiation device and before a radiation procedure by an imaging process wherein initial coordinate points along a laser line projected on the surface of the patient were determined by the evaluation and control apparatus based on initial measurement values detected by a camera through the real-time triangulation process, and the initial coordinate points were saved as target coordinate points in the memory device.

5. The system according to claim 1, further comprising: a display device connected to the evaluation and control apparatus and controlled to show at least one of the first coordinate points determined during the first radiation treatment procedure or the target coordinate points in real time.

6. The system according to claim 1, wherein the evaluation and control apparatus is configured to at least one of emit a warning signal in the case of an impermissible deviation between the first coordinate points and the target coordinate points or perform a correction of a position of the patient by activating movement control of the patient table.

7. The system according to claim 1, wherein the evaluation and control apparatus is configured to determine point coordinates of two laser lines intersecting at an intersection of a central beam of a radiation device with the surface of the patient and to determine a focus-skin distance using the point coordinates, wherein focus-skin distance is a distance of a focal point of the radiation device to a surface of the patient along a vector from the focal point to an isocenter of a coordinate system of the radiation device.

8. The system according claim 1, wherein at least one of the several room lasers projects a laser line onto at least one of a surface of the patient table or a radiation device for the first radiation treatment procedure, wherein the at least one camera detects the laser line projected onto the at least one of the surface of the patient table or the radiation device, and wherein the evaluation and control apparatus is configured to determine coordinate points along the laser line projected onto the at least one of the surface of the patient table or the radiation device during the first radiation treatment procedure based on the measurement values detected by the at least one camera through a real-time triangulation process.

9. The system according to claim 1, wherein the several room lasers comprises at least four room lasers, two of which are lateral room lasers arranged on opposite-lying sides of the patient table and project respectively one lateral horizontal laser line and one transverse line onto the patient, and at least two of which are arranged above the patient table, a first of which projects at least one transversal line onto the patient and a second of which projects a longitudinal line onto the patient.

10. The system according to claim 9, characterized in that each of the two lateral room lasers comprises respectively two laser sources, a first laser source that projects the lateral horizontal laser line and a second laser source that projects the transverse line.

11. The system according to claim 9, wherein the at least one camera comprises at least two cameras respectively configured to detect the laser lines projected by at least two of the at least four room lasers.

12. A method for determining the position of objects in a radiation treatment room for radiation therapy, comprising:
  detecting, using at least one camera, at least one laser line projected onto a surface of a patient positioned on a patient table by at least one laser;
  determining coordinate points along the at least one laser line projected onto the surface of the patient during a radiation procedure based on measurement values detected by the camera through a real-time triangulation process;
  determining target coordinate points based on a computed-tomography (CT) image of the patient or on another reference image process before a radiation treatment procedure from intersection coordinate points of the surface of the patient determined within a framework of the CT image or another reference image process with two or three planes located perpendicular to each other and intersecting in a center of an area of the patient;
  storing the target coordinate points;
  comparing the determined coordinate points with the target coordinate points for patient positioning during the radiation treatment procedure; and
  saving the determined coordinate points for documentation of the radiation treatment procedure.

13. The method according to claim 12, further comprising at least one of:
  emitting a warning signal in a case of an impermissible deviation between the determined coordinate points and the target coordinate points; or
  performing a correction of a position of the patient by activating movement control of the patient table.

14. The method according to claim 12, further comprising:
  capturing a breathing movement or another type of movement of the patient during the radiation treatment procedure.

15. The method according to claim 14, further comprising:
  controlling a radiation device such that radiation only takes place in a specified breathing position or other position of the patient.

16. The method according to claim 12, further comprising:
  determining point coordinates of two laser lines intersecting at an intersection of a central beam of a radiation device with the surface of the patient are determined; and
  determining a focus-skin distance using the point coordinates, wherein focus-skin distance is a distance of a focal point of the radiation device to a surface of the patient along a vector from the focal point to an isocenter of a coordinate system of the radiation device.

17. The method according to claim 12, further comprising:
  projecting a laser line onto at least one of a surface of the patient table or a radiation device;
  detecting, using the at least one camera, measurement values of the laser line projected onto the at least one of the surface of the patient table or the radiation device;
  determining, through a real-time triangulation process, coordinate points along the laser line projected onto the at least one of the surface of the patient table or the radiation device during the radiation treatment procedure based on the measurement values detected by the at least one camera.

18. The method according to claim 17, further comprising at least one of:
  comparing the coordinate points along the laser line projected onto the at least one of the surface of the patient table or a radiation device with target coordinate points and emitting a warning signal in the case of an impermissible deviation between the determined coordinate points and the target coordinate points; or
  saving the determined coordinates points by saving the coordinate points along the laser line projected onto the at least one of the surface of the patient table or the radiation device for document of the radiation treatment procedure.

19. The method according to claim 12, further comprising:
modifying a target dose within a subsequent radiation treatment procedure of the patient using the saved coordinate points.

* * * * *